United States Patent [19]
Woodward et al.

[11] 4,102,335
[45] Jul. 25, 1978

[54] MALE POTENCY DEVICE

[76] Inventors: Robert John Woodward, 29 Calfside, Cheam, Surrey; Walter O'Connell, 63 Garden Ave., Mitcham, Surrey, both of England

[21] Appl. No.: 755,072

[22] Filed: Dec. 28, 1976

[30] Foreign Application Priority Data

Dec. 30, 1975 [GB] United Kingdom ............... 53156/75

[51] Int. Cl.² .............................................. A61F 5/00
[52] U.S. Cl. ...................................... 128/68.1; 128/79
[58] Field of Search .................. 128/79, 68.1, 384–388

[56] References Cited
U.S. PATENT DOCUMENTS

| | | | |
|---|---|---|---|
| 371,521 | 10/1887 | Rowell | 128/79 |
| 522,841 | 7/1894 | Lawlor | 128/386 |
| 609,614 | 8/1898 | Doty | 128/79 |
| 1,043,187 | 11/1912 | Yount | 128/79 |
| 2,576,024 | 11/1951 | Laser | 128/79 |
| 3,612,047 | 10/1971 | Nesbit | 128/79 |

FOREIGN PATENT DOCUMENTS

| | | | |
|---|---|---|---|
| 194,449 | 3/1923 | United Kingdom | 128/386 |
| 214,654 | 6/1925 | United Kingdom | 128/79 |

*Primary Examiner*—Lawrence W. Trapp
*Attorney, Agent, or Firm*—Hopgood, Calimafde, Kalil, Blaustein & Lieberman

[57] ABSTRACT

A male potency device comprises a ring member adapted to surround the male genitalia having at least one pair of metallic surfaces of metals having different electrode potentials on its internal circumference, said surface being adapted to remain in contact with the male genitalia when the device is worn; and adjusting means whereby the circumference of the ring member may be varied. Preferred adjusting means comprises a rotatable section of the ring member which is rotatable with respect to the ring member and is maintained in engagement therewith by at least one screw coupling, the degree of rotation of the screw coupling(s) serving to determine the variation in circumference of the ring member.

17 Claims, 2 Drawing Figures

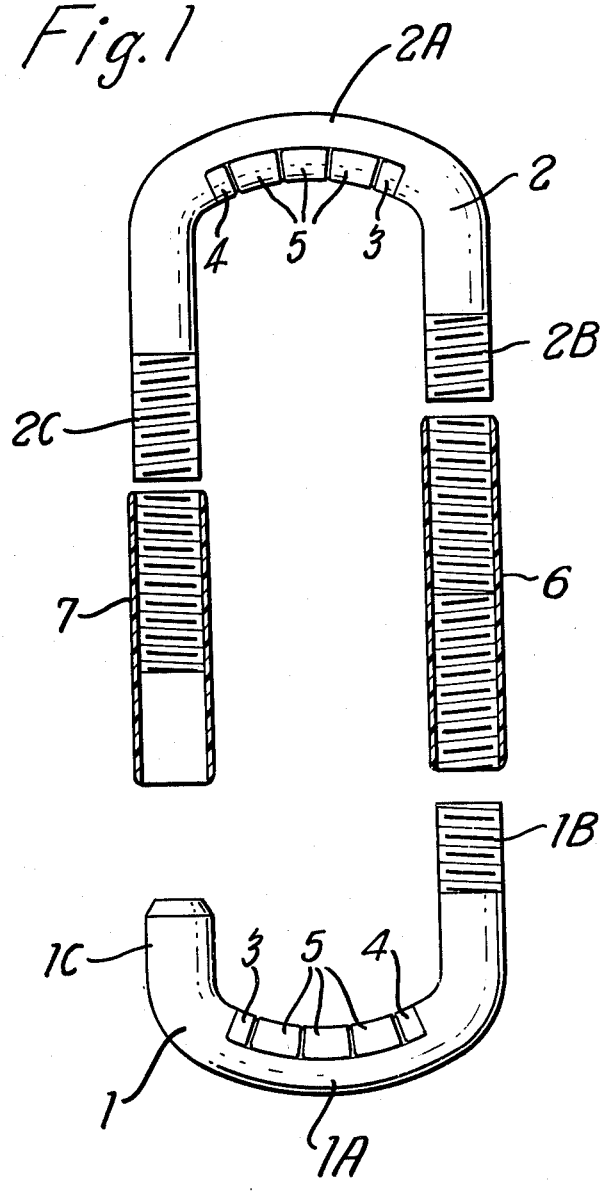

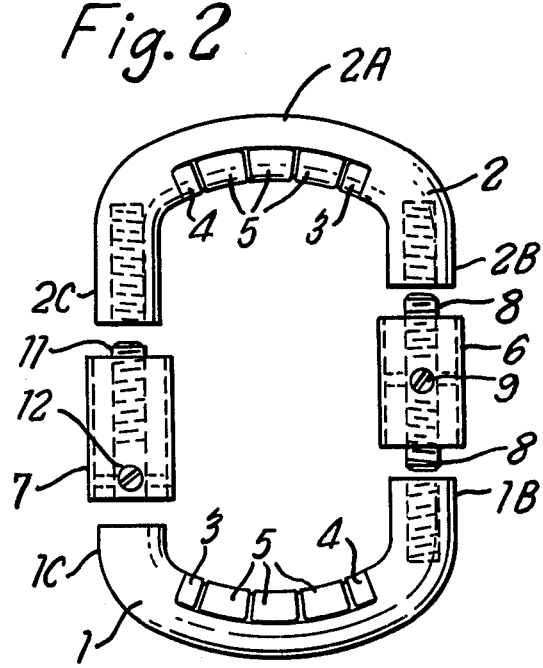

MALE POTENCY DEVICE

This invention relates to male potency devices of the type comprising a ring member adapted to maintain at least one pair of metallic surfaces, each surface having a different electrode potential, in contact with the male genitalia.

Known such devices comprise a ring member having two straight parallel sides and two outwardly curved sides, each side being of circular cross-section. The internally-facing surfaces of the curved sides each have inset in them a strip of copper and a strip of zinc. The ring is used by being placed around the genitalia, against the body wall, with the straight sides vertical and the strips being lightly in contact with the skin of the scrotum on the lower side of the penis on the upper side.

It has been demonstrated that such devices heighten male potency and, as either a consequent or an independent effect, increase nervous and psychological energy generally. It has been suggested that the efficacy of the devices derives from minute electrical currents flowing between the metallic surfaces of differing electrode potential, the necessary electrical conductivity being provided by perspiration, but the physiological factors involved are not properly understood. But whatever the nature of the devices' effect — and, indeed, even if that effect is purely psychological — the tens of thousands of the devices which have been sold throughout the world over a period of nearly 50 years have undoubtedly brought about real results and contributed to the well-being of large numbers of people.

A difficulty with the said devices of known type, which has never been satisfactorily overcome, lies in the method by which they are to be put on. In order to remain in position during wear, the devices have to be a slightly tight fit so that they cannot comfortably be donned merely by being slid over the relevant parts of the body. Known devices therefore comprise means whereby a section of one of the straight sides may be partially removed to open the ring and facilitate its putting on. The section is then replaced. However, the removable section is held in position in the ring member by means of a metallic clip, the opening and closing of which when the device is in position carries a danger of pinching or causing other discomfort. Various suggestions to overcome this problem by altering the nature of the clip have been unsuccessful.

The present invention provides a male potency device comprising a ring member adapted to surround the male genitalia having at least one pair of metallic surfaces of metals having different electrode potentials on its internal circumference, said surfaces being adapted to remain in contact with the male genitalia when the device is worn, and adjusting means whereby the circumference of the ring member may be varied.

Preferably, the novel device comprises two pairs of metallic surfaces adapted to remain in contact with the upper side of the penis and the lower side of the scrotum respectively during wear.

The ring member may be rigid, flexible or may comprise both rigid and flexible sections. Preferably the ring member is rigid throughout. The adjusting means may comprise a first adjusting means whereby the circumference of the ring member may be varied by a predetermined amount and, situated substantially opposite the first adjusting means on the circumference of the ring member, a second adjusting means adapted to bring about a like variation in the circumference of the ring member to that brought about by operation of the first adjusting means. In this way the relative positions of any two pairs of electrode surfaces on the circumference of the ring member may be kept the same regardless of any variations in the length of the circumference.

Such a first adjusting means preferably comprises a rotatable section of the ring member which is rotatable with respect to the ring member being maintained in engagement therewith by at least one screw coupling, the degree of rotation of the screw coupling serving to determine the variation in circumference of the ring member.

Preferably, the rotatable section is screw-threaded at both ends and in different senses and co-operates with screw-threads in adjacent portions of the ring member. The ends of the rotatable section may overlap the adjacent ends of the ring member or alternatively may be housed therein.

Alternatively, the rotatable section may engage with the ring member at at least one of its ends by means of a shaft member extending axially beyond the rotatable section at at least one of its ends, said shaft member being screw-threaded at least at its end so as to be engageable with a screw-threaded axial passage in the adjacent portion of the ring member.

Said second adjusting means may comprise a sleeve portion of the circumference of the ring member which slideably engages an adjacent portion of the ring member. Preferably the sleeve portion is a cylindrical member engaging the adjacent portions of the ring member by a screw coupling at one end and by a slideable sleeve engagement at its other end.

The screw coupling by which the sleeve member engages one adjacent portion of the ring member may comprise a shaft member extending axially beyond the sleeve member and being screw-threaded at least at its end so as to be engageable with a screw-threaded axial passage in the adjacent portion of the ring member.

In a preferred form the present invention provides a male potency device which comprises a ring member comprising at least one pair of metallic surfaces of metal having different electrode potentials on its internal circumference and two straight sides; a first straight side comprising a first adjusting means consisting of a cylindrical section internally screw-threaded at both ends so as to co-operate with screw threads at the adjacent end-parts of the first straight side; the hands of the screw-threads on the cylindrical section being of different senses; and a second straight side comprising a second adjusting means whereby the length of the second straight side may be adjusted.

Alternatively, the first adjusting means may engage with the adjacent portions of the first straight side by means of internal male-female screw couplings, threaded in opposite senses.

The materials of construction of the novel devices, their external dimensions and the nature and dispositions of the metallic surfaces may be as in previous such devices. The metallic surfaces are preferably of zinc and copper and of areas from 50 to 80 sq. mms. With metals other than zinc and copper the areas of the metallic surfaces may need to be varied for optimum effect and the appropriate areas may be determined by routine experiment. The ring member is preferably of ebonite with a circular cross-section of approximate diameter 7-12 mms.

The size of the ring member of the preferred novel device may be adjusted by rotating the cylindrical section so as to increase or decrease the distance between the adjacent end-parts of the first straight side, so lenghening or shortening the first straight side. This automatically brings about a corresponding variation in the length of the second straight side. In the preferred form of the adjusting means described above this automatic variation is brought about by movement of the sleeve section over the non-screw-threaded end portion of the second straight side. By this means the ring member may be expanded sufficiently to be placed over the parts of the body without discomfort and subsequently contracted to a size giving a comfortable but secure fit.

In a preferred form of the device, the length of the second straight side may be increased by the adjusting means beyond the maximum possible length of the first straight side thus permitting the cylindrical section to be detached completely from the device, further facilitating its placement.

An advantage of the novel device is that its adjustable size avoids or reduces the need for a range of devices of different, unalterable, sizes which have hitherto been required in order to cater for variations in the relevant bodily dimensions of either individual or different wearers.

Preferred embodiments of the invention will now be described with reference to the accompanying drawings FIGS. 1 and 2, which are exploded plan views.

The preferred embodiment of FIG. 1 comprises two sections 1 and 2 having curved portions 1A and 2A and straight portions 1B and 1C and 2B and 2C. Portions 1 and 2 are of non-toxic ebonite and are of circular cross-section, diameter approximately 9 mms.

The ends of portions 1B and 2B are screw-threaded in different senses. The end of portion 2C is also screw-threaded. The end of portion 1C is chamfered.

The curved portions 1A and 2A carry inset metallic strips 3, 4 and 5 of arcuate cross-section. Strips 3 and 4 are of copper and zinc respectively and have approximate dimensions 4 by 17 mms. Strips 5 are of brass and are of approximate dimensions 20 by 5 mms.

Between end portions 1B and 2B is a removable central cylindrical section 6, internally screw-threaded at its ends to engage with the screw-threads on portions 1B and 2B.

Between end portions 1C and 2C is a sleeve section 7 internally screw-threaded at one end to engage with the screw-thread on portion 2C. At its other end sleeve section 7 slideably covers end portion 1C.

The preferred embodiment of FIG. 2 comprises two sections 1 and 2 having curved portions 1A and 2A and straight portions 1B and 1C and 2B and 2C. Portions 1 and 2 are of non-toxic ebonite and are of circular cross-section, diameter approximately 9 mms.

The end portions of 1B and 2B are internally axially screw-threaded in different senses.

Between end portions 1B and 2B is a removable central cylindrical section 6, containing an axially extending metallic shaft 8 screw-threaded in opposite senses at its ends. Shaft 8 is engageable with the internal screw-threads in portion 1B and portion 2B. Shaft 8 is maintained in position inside section 6 by means of a screw 9 passing through shaft 8 at right angles to it and secured in position by counter-sunk heads at each end.

Between end portions 1C and 2C is a sleeve section 7 containing at its end adjacent portion 2C an axially extending metal shaft 11 screw-threaded at its end so as to be engageable with the internal screwthread in portion 2C. Shaft 11 is maintained within sleeve section 7 by a screw 12 similar to screw 9.

In both the preferred embodiments described by rotating cylindrical section 6 the displacement of sections 1 and 2 and the side of the device, can be varied as required during the fitting operation. It is also possible to completely unscrew cylindrical section 6 so as to remove it altogether from the device, further facilitating fitting.

We claim:

1. A male potency device, comprising a ring member adapted to surround the male genitalia and comprising a first straight side and a second straight side separated by curved sides, at least one pair of metallic surfaces of metals having different electrode potentials located on an internal circumference of the ring member and adapted to remain in contact with the male genitalia when the device is worn, a first adjusting means incorporated in the first straight side whereby the circumference of the ring member may be varied by a predetermined amount, and a second adjusting means incorporated in the second straight side and adapted to bring about a like variation in the circumference of the ring member to that brought about by operation of the first adjusting means.

2. A device as claimed in claim 1 which comprises two pairs of metallic surfaces adapted to remain in contact with the upper side of the penis and the lower side of the scrotum respectively during wear.

3. A device as claimed in claim 1 wherein the first adjusting means comprises a rotatable section of the ring member which is rotatable with respect to the ring member and is maintained in engagement therewith by at least one screw coupling, the degree of rotation of the screw coupling (s) serving to determine the variation in circumference of the ring member.

4. A device as claimed in claim 3 wherein the rotatable section is screw-threaded at both ends and in different senses and co-operates with screw-threads in adjacent portions of the ring member.

5. A device as claimed in claim 3 wherein the rotatable section engages with the adjacent portion of the ring member by means of internal male and female screw couplings.

6. A device as claimed in claim 5 wherein the rotatable section engages with the ring member at at least one of its ends by means of a shaft member extending axially beyond the rotatable section at at least one of its ends, said shaft member being screw-threaded at least at its end so as to be engageable with a screw-threaded axial passage in the adjacent portion of the ring member.

7. A device as claimed in claim 6 wherein the second adjusting means comprises a sleeve portion of the circumference of the ring member which slideably engages an adjacent portion of the ring member.

8. A device as claimed in claim 7 wherein the sleeve portion is a substantially cylindrical member engaging the adjacent portions of the ring member by a screw coupling at one end and by a slideable sleeve engagement at its other end.

9. A device as claimed in claim 1 wherein the second adjusting means comprises a sleeve portion of the circumference of the ring member which slideably engages an adjacent portion of the ring member.

10. A device as claimed in claim 5 wherein the sleeve portion is a substantially cylindrical member engaging the adjacent portions of the ring member by a screw coupling at one end and by a slideable sleeve engagement at its other end.

11. A device according to claim 1 which comprises a ring member comprising at least one pair of metallic surfaces of metals having different electrode potentials on its internal circumference and two straight sides; a first straight side comprising a first adjusting means consisting of a cylindrical section internally screw-threaded at both ends so as to co-operate with screw-threads at the adjacent end-parts of the first straight side; the hands of the screw-threads on the cylindrical section being of different senses; and a second straight side comprising a second adjusting means whereby the length of the second straight side may be adjusted.

12. A device as claimed in claim 11 wherein the length of the second straight side may be increased by the adjusting means beyond the maximum possible length of the first straight side thus permitting the cylindrical section to be detached completely from the device.

13. A device as claimed in claim 11 in which the second adjusting means comprises a sleeve portion of the second straight side which slideably engages an adjacent portion of the second straight side.

14. A device as claimed in claim 13 wherein the sleeve portion engages the adjacent portions of the second straight side by a screw-coupling at one end and by a slideable sleeve engagement at the other end.

15. A device as claimed in claim 1, wherein the second adjusting means is situated substantially opposite the first adjusting means.

16. A male potency device, comprising a ring member adapted to surround the male genitalia and comprising first and second multiple-part straight generally parallel sides separated by end-connecting sides, at least one pair of metallic surfaces of metals having different electrode potentials located on an internal surface region of the ring member and adapted to remain in contact with the male genitalia when the device is worn, each end-connecting side being unit-handling with at least a part of each of the straight sides, and at least two of the parts of each of the straight sides having telescoping interfit whereby the length between end-connecting sides may be selectively adjusted to vary the peripheral extent of the ring member by a predetermined amount.

17. A device as claimed in clain 16, wherein the two telescopically interfitted parts of one straight side have a longitudinally sliding interfit relation, and wherein the two telescopically interfitted parts of the other straight side have a threaded interfit relation.

* * * * *